United States Patent
Choi et al.

(10) Patent No.: US 9,532,934 B2
(45) Date of Patent: Jan. 3, 2017

(54) COSMETIC COMPOSITION CARRIER COMPRISING FOAMS

(71) Applicant: AMOREPACIFIC CORPORATION, Seoul (KR)

(72) Inventors: Jung Sun Choi, Yongin-si (KR); Kyung Nam Kim, Yongin-si (KR); Kyung Ho Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/391,076

(22) PCT Filed: Apr. 12, 2013

(86) PCT No.: PCT/KR2013/003100
§ 371 (c)(1),
(2) Date: Oct. 7, 2014

(87) PCT Pub. No.: WO2013/154391
PCT Pub. Date: Oct. 17, 2013

(65) Prior Publication Data
US 2015/0118269 A1    Apr. 30, 2015

(30) Foreign Application Priority Data

Apr. 13, 2012  (KR) .................. 10-2012-0038471

(51) Int. Cl.
| | |
|---|---|
| *A61K 8/87* | (2006.01) |
| *A61Q 1/00* | (2006.01) |
| *A61Q 1/02* | (2006.01) |
| *A61Q 19/00* | (2006.01) |
| *A45D 33/00* | (2006.01) |
| *A61K 8/04* | (2006.01) |
| *A45D 37/00* | (2006.01) |
| *A61K 8/02* | (2006.01) |
| *A61Q 17/04* | (2006.01) |
| *A61K 8/81* | (2006.01) |

(52) U.S. Cl.
CPC .............. *A61K 8/046* (2013.01); *A45D 37/00* (2013.01); *A61K 8/0208* (2013.01); *A61K 8/8194* (2013.01); *A61K 8/87* (2013.01); *A61Q 1/02* (2013.01); *A61Q 17/04* (2013.01); *A61Q 19/00* (2013.01)

(58) Field of Classification Search
None
See application file for complete search history.

(56) References Cited

U.S. PATENT DOCUMENTS

| | | |
|---|---|---|
| 6,883,995 B1 | 4/2005 | Gueret |
| 2002/0025211 A1 | 2/2002 | Gueret |
| 2007/0253914 A1 | 11/2007 | Ha et al. |
| 2008/0083419 A1* | 4/2008 | Glenn et al. ............. 132/208 |
| 2010/0260701 A1* | 10/2010 | Dop ..................... 424/78.03 |
| 2011/0014254 A1 | 1/2011 | Choi et al. |

FOREIGN PATENT DOCUMENTS

| | | |
|---|---|---|
| CN | 101522070 | 9/2009 |
| JP | 08024041 | 1/1996 |
| JP | 2002125755 | 5/2002 |
| JP | 200312457 | 1/2003 |
| KR | 1020000013194 | 3/2000 |
| KR | 200406826 | 1/2006 |
| KR | 100550418 | 2/2006 |
| KR | 1020090100643 | 9/2009 |
| WO | 2008044200 | 4/2008 |
| WO | 2012128589 | 9/2012 |

OTHER PUBLICATIONS

Recticel, "Filtration," <http://www.recticel.fi/suodatinmateriaalit.htm>, retrieved May 7, 2015, p. 1-4.*
FDA, "Is It a Cosmetic, a Drug, or Both? (or Is It Soap?)," <http://www.fda.gov/Cosmetics/GuidanceRegulation/LawsRegulations/ucm074201.htm>, Updated Mar. 24, 2015, p. 1-8.*
International Search Report—PCT/KR2013/003100 dated Jun. 26, 2013.
Written Opinion—PCT/KR2013/003100 dated Jun. 26, 2013.
European Search Report—EP Application No. 137755072.5 dated Nov. 2, 2015, citing US2007253914 and WO2012/128589.
Chinese Office Action-Chinese Application No. 201380031646.X dated Jan. 4, 2016, citing CN101522070.

* cited by examiner

*Primary Examiner* — Tracy Vivlemore
*Assistant Examiner* — Monica Shin
(74) *Attorney, Agent, or Firm* — Cantor Colburn LLP

(57) ABSTRACT

The present invention relates to a cosmetic composition carrier in which one or more foams having a number of pores in the range of 10 ppi to 130 ppi are impregnated with a cosmetic composition having a viscosity of 1,000 to 5,000 cps and 15,000 to 100,000 cps so as to enable a user to carry a compact type liquid cosmetic composition.

8 Claims, No Drawings

COSMETIC COMPOSITION CARRIER COMPRISING FOAMS

TECHNICAL FIELD

The present disclosure relates to a cosmetic composition carrier comprising one or more foam.

BACKGROUND ART

A liquid cosmetic composition is commonly provided as stored in a vacuum container, a pump container or a glass container. However, these containers are inconvenient to carry. Recently, as the necessity of putting on or adjusting makeup outdoors increases, there is a need of a liquid cosmetic composition that can be carried conveniently.

A compact-type container may be considered as a container capable of conveniently carrying a liquid cosmetic composition. In order to hold a liquid cosmetic composition in the compact-type container, it should be considered whether container is compatible with the cosmetic composition, whether the cosmetic composition can be effectively filled in the carrier, whether the carrier can impregnate the cosmetic composition stably for a long time, and whether an adequate amount of the cosmetic composition can be ejected from the carrier.

The inventors of the present disclosure have found out that a cosmetic composition carrier comprising one or more foam has superior filling ability, impregnating ability and discharging ability.

DISCLOSURE

Technical Problem

The present disclosure is directed to providing a cosmetic composition carrier which is convenient to use.

Technical Solution

In one general aspect, the present disclosure provides a cosmetic composition carrier comprising one or more foam having 10-130 pores per inch (ppi).

Advantageous Effects

A cosmetic composition carrier of the present disclosure can effectively fill a cosmetic composition, impregnate the cosmetic composition stably for a long time, allows ejection of an adequate amount of the cosmetic composition and maintains superior durability in the state where the cosmetic composition is impregnated. Accordingly, the cosmetic composition carrier of the present disclosure allows convenient makeup outdoors since even a liquid cosmetic composition can be carried conveniently.

BEST MODE

As used herein, a "carrier" refers to a material capable of holding any substance or component which may be a composition. It can also be expressed as a "medium". As used herein, "impregnating ability" refers to the ability to hold and carry any substance or component.

As used herein, a "foam" refers to a polymer foamed by dry or wet foaming. The foam used in the present disclosure has a large pore size, high air permeability and superior cushioniness, softness, flexibility and elasticity. Further, the foam of the present disclosure may have superior filling ability of absorbing a cosmetic composition, excellent impregnating ability of holding the cosmetic composition stably for a long time, good discharging ability of ejecting an adequate amount of the cosmetic composition and superior durability even in the state where the cosmetic composition is impregnated.

As used herein, "hardness measured with an Asker hardness tester type F" refers to the hardness of a foam measured using an Asker Durometer hardness tester type F before impregnating a composition.

As used herein, "flocking" refers to a process of depositing very short fibers (flock) onto, e.g., a foam.

In an aspect, the present disclosure provides a cosmetic composition carrier comprising one or more foam having 10-130 pores per inch (ppi). In the present disclosure, the "number of pores" means the number of pores per inch of a urethane foam. The number of pores may mean an average number of pores per inch of a horizontal or vertical line measured according to WI-QA-14 (ASTM).

If the number of pores of the foam is smaller than 10 ppi, impregnating ability may be unsatisfactory. And, if it exceeds 130 ppi, filling ability and discharging ability may be unsatisfactory. In this regard, the foam of the present disclosure may have 40-170 ppi, 50-160 ppi, 60-150 ppi, 70-140 ppi or 60-130 ppi, specifically 60-90 ppi.

More specifically, the foam having a number of pores of 10-130 ppi has a hardness measured with an Asker hardness tester type F of 10-100. If the foam has a hardness lower than 10, a content may not be impregnated uniformly and the cosmetic composition may be ejected excessively. And, if the hardness is greater than 100, it is difficult to fill and eject the cosmetic composition. In this regard, the foam may have a hardness measured with an Asker hardness tester type F of 20-90, 30-80, 40-70 or 50-60.

In the cosmetic composition carrier according to the present disclosure, the foam may have a number of pores of 60-90 ppi and the carrier may be for impregnating a cosmetic composition having a viscosity of 15000-30000 centipoise (cps).

For impregnating a cosmetic composition having a viscosity of 15000-30000 cps, it is desired that the foam has a number of pores of 60-90 ppi. A foam having the above-described number of pores has superior ability of filling and discharging the cosmetic composition and also has very superior impregnating ability. More specifically, the foam has more superior impregnating ability, filling ability and discharging ability for a cosmetic composition having a viscosity of 15000-30000 cps when the foam has a density of 1.2-2.2 lb/ft$^3$, a hardness measured with an Asker hardness tester type F of 70-90 and a cell size of 100-400 μm.

In the cosmetic composition carrier according to the present disclosure, the foam may have a number of pores of 10-30 ppi and the carrier may be for impregnating a cosmetic composition having a viscosity of 60000-100000 cps. For example, the cosmetic composition may be a cake-type cosmetic composition or a solid cosmetic composition. For impregnating a cosmetic composition having a viscosity of 60000-100000 cps, it is desired that the foam has a number of pores of 10-30 ppi. A foam having the above-described number of pores has superior ability of impregnating and discharging the cosmetic composition. More specifically, the foam has more superior impregnating ability and filling ability for a cosmetic composition having a viscosity of 60000-100000 cps when the foam has a density of 1.7-2.0 lb/ft³, a hardness measured with an Asker hardness tester type F of 10-30 and a cell size of 100-400 μm.

In the cosmetic composition carrier according to the present disclosure, the foam may have a number of pores of 30-60 ppi and the carrier may be for impregnating a cosmetic composition having a viscosity of 30000-60000 cps.

For impregnating a cosmetic composition having a viscosity of 30000-60000 cps, it is desired that the foam has a number of pores of 30-60 ppi. A foam having the above-described number of pores has superior filling ability, impregnating ability and discharging ability. More specifically, the foam has more superior impregnating ability, filling ability and discharging ability for a cosmetic composition having a viscosity of 30000-60000 cps when the foam has a density of 1.7-2.1 lb/ft³, a hardness measured with an Asker hardness tester type F of 30-60 and a cell size of 100-400 μm.

In the cosmetic composition carrier according to the present disclosure, the foam may have a number of pores of 90-130 ppi and the carrier may be for impregnating a cosmetic composition having a viscosity of 1000-5000 cps. Specifically, the cosmetic composition may have a viscosity of 1000-5000 cps, 2000-5000 cps or 3000-5000 cps.

For impregnating a cosmetic composition having a viscosity of 1000-5000 cps, it is desired that the foam has a number of pores of 90-130 ppi. A foam having the above-described number of pores has very superior impregnating ability. More specifically, the foam has more superior filling ability, impregnating ability and discharging ability for a cosmetic composition having a viscosity of 1000-5000 cps when the foam has a density of 4.0-6.6 lb/ft³, a hardness measured with an Asker hardness tester type F of 100-120 and a cell size of 100-400 μm.

The density may be measured according to ASTM D3574, but is not limited thereto. The viscosity may be measured using a viscometer, for example, LVDV II+PRO or RVDV III ULTRA, spindle No. 63 or spindle No. 64, at 5 rpm or 12 rpm, but is not limited thereto.

In the cosmetic composition carrier according to the present disclosure, the foam may include one or more selected from a group consisting of butadiene rubber (BR), styrene-butadiene rubber (SBR), natural rubber (NR), wet urethane, dry urethane, polyether, polyester, polyvinyl chloride, polyethylene, ethylene-vinyl acetate (EVA), latex, silicone, styrene-isoprene-styrene (SIS), styrene-ethylene-butylene-styrene (SEBS), polyvinyl alcohol (PVA), silicone elastomer, nitrile rubber, butyl rubber and neoprene.

In the cosmetic composition carrier according to the present disclosure, the foam may have a cell size of 50-2500 μm.

If the pore size is smaller than 50 μm, filling ability and discharging ability are unsatisfactory. And, if the pore size exceeds 2500 μm, filling ability is good but impregnating ability and discharging ability are unsatisfactory. In this regard, the foam may have a cell size of 75-2200 μm, 100-2000 μm, 125-1800 μm, 150-1600 μm, 175-1500 μm or 200-1400 μm, specifically, 200-1200 μm. In an exemplary embodiment of the present disclosure, the "pore size (cell size)" may be measured using an optical microscope (Nikon Eclipse 80i).

In the cosmetic composition carrier according to the present disclosure, the foam may have a thickness of 5-30 mm.

If the thickness of the foam is smaller than 5 mm, the amount of the cosmetic composition that can be impregnated decreases. And, if the thickness exceeds 30 mm, some of the content may remain without being completely ejected. In this regard, the foam of the present disclosure may have a thickness of 6-29 mm, 7-28 mm, 8-27 mm, 9-26 mm or 10-25 mm.

In the cosmetic composition carrier according to the present disclosure, the foam may be flocked with cotton, cotton/acryl, cotton/acryl/polyester, cotton/rayon, acryl, polyamide, nylon, polyester, nylon/polyester or silk.

The symbol "/" represents that two materials are used together. For example, "cotton/acryl" means that the foam is flocked with a mixture of cotton and acryl. In the present disclosure, the mixing ratio of the two materials may be 0.1-10:1, 1-9:1, 2-8:1 or 3-7:1 based on weight.

In the cosmetic composition carrier according to the present disclosure, the foam may be flocked with a fiber of 0.6-1.5 Denier×0.6-1.0 mm. A uniform flocking can be achieved when the fiber has the above-described diameter and length. Specifically, the foam may be flocked with a fiber of 0.6 Denier×0.6 mm, 0.8 Denier×0.8 mm, 1.5 Denier×0.8 mm, 1 Denier×1.0 mm, 1.5 Denier×1.0 mm or 1.0 Denier×0.8 mm, but is not limited thereto. The "Denier" is a unit of measure for the thickness of a fiber and is often denoted as d or D. 1 Denier is defined as unit weight of 0.05 g per standard length of 450 m. That is to say, the denier is calculated by the equation $D=(L/W)\times(w/l)$ (L: standard length, W: unit weight, w: fiber weight, l: fiber length). Accordingly, the denier is larger as the fiber is heavier and thicker and is smaller as the fiber is lighter and thinner.

In the cosmetic composition carrier according to the present disclosure, the cosmetic composition may be in liquid or solid state.

In the cosmetic composition carrier according to the present disclosure, the cosmetic composition may be solution, emulsion, gel, cream or suspension.

In general, a liquid cosmetic composition is difficult to carry and store than a solid cosmetic composition. However, if the cosmetic composition carrier according to the present disclosure is used, even a cosmetic composition in liquid or cream state can be stored and carried stably and safely. If the cosmetic composition is in solid state, instant change in physical properties due to heat or external impact can be reduced by impregnating the solid cosmetic composition in the carrier and an adequate amount of the content can be ejected from the carrier. In another exemplary embodiment of the present disclosure, the cosmetic composition may be solution, emulsion or suspension, but is not limited thereto.

The cosmetic composition that can be used for the cosmetic composition carrier according to the present disclosure may be an emulsion composition, specifically a water-in-oil (W/O) or oil-in-water (O/W) composition or a dispersion composition, specifically an oily dispersion or an aqueous dispersion.

The cosmetic composition may be formulated as, for example, makeup primer, makeup base, liquid or solid foundation, concealer, lipstick, lip gloss, powder, lip liner, eyebrow, eye shadow, blusher, twin cake, sunscreen, lotion, cream, essence, etc., but is not limited thereto.

The cosmetic composition carrier according to the present disclosure may be provided as a container for a cosmetic product which includes a lower portion for accommodating the cosmetic product and an upper portion having a cover and, optionally, a mirror, which is usually called a compact.

Hereinafter, the present disclosure will be described in detail through examples, comparative examples and test examples. However, the following examples, comparative examples and test examples are for illustrative purposes only and it will be apparent to those of ordinary skill in the art that the scope of the present disclosure is not limited by the examples.

Example 1

A foam made of dry polyurethane and having a number of pores of 20 ppi was used. The foam had a density of 1.8 lb/ft$^3$, a hardness measured with an Asker hardness tester type F of 10 and a cell size of 350 μm. The hardness was one before impregnating a cosmetic composition. The number of pores was measured by counting and averaging the number of pores per inch of a horizontal or vertical line according to WI-QA-14 (ASTM). The density was measured according to ASTM D3574 and the cell size was measured using an optical microscope (Nikon Eclipse 80i).

Example 2

A foam made of NBR and having a number of pores of 45 ppi was used. The foam had a density of 2.0 lb/ft$^3$, a hardness measured with an Asker hardness tester type F of 40 and a cell size of 350 μm. The measurements were made in the same manner as in Example 1.

Example 3

A foam made of NBR and having a number of pores of 75 ppi was used. The foam had a density of 2.2 lb/ft$^3$, a hardness measured with an Asker hardness tester type F of 80 and a cell size of 250 μm. The measurements were made in the same manner as in Example 1.

Example 4

A foam made of wet urethane and having a number of pores of 110 ppi was used. The foam had a density of 5.3 lb/ft$^3$, a hardness measured with an Asker hardness tester type F of 100 and a cell size of 150 μm. The measurements were made in the same manner as in Example 1.

The characteristics of the foams of Examples 1-4 were investigated in Test Examples. A cosmetic composition to be absorbed in each foam was prepared as follows.

Preparation Example

Preparation of Cosmetic Compositions

Cosmetic composition containing oily components, emulsifying agents, an organic or inorganic anti-UV agent, pigments and aqueous components were prepared as described in Table 1.

TABLE 1

|  |  | Components (wt %) | Ex. 1 | Ex. 2 | Ex. 3 | Ex. 4 |
|---|---|---|---|---|---|---|
| Oily components | Oily components | Ozokerite | 10.0 | 10.0 | 5.0 | 1.0 |
|  |  | Dicaprylyl carbonate | 10.00 | 10.00 | 10.00 | 10.00 |
|  | Anti-UV agent | Octyl methoxycinnamate | 7.000 | 7.000 | 7.000 | 7.000 |
|  | Thickener | Disteardimonium hectorite | 3.00 | 2.00 | 1.50 | 1.50 |
|  | Oily components | Decamethylcyclopentasiloxane | 16.00 | 16.00 | 16.00 | 16.00 |
|  | Emulsifying agents | Sorbitan sesquioleate | 2.000 | 2.000 | 2.000 | 2.000 |
|  |  | Lauryl PEG/PPG-18/18 methicone | 1.500 | 1.500 | 1.500 | 1.500 |
|  | Pigments | Poly(methyl methacrylate) | 5.00 | 5.00 | 5.00 | 5.00 |
|  |  | Titanium dioxide/iron oxide | 7.00 | 7.00 | 7.00 | 7.00 |
| Aqueous components |  | Water | To 100 | To 100 | To 100 | To 100 |
|  | Humectant | Glycerine | 8.000 | 8.000 | 8.000 | 8.000 |
|  | Emulsification stabilizer | Salt | 1.00 | 1.00 | 1.00 | 1.00 |
|  |  | Flavor | 0.200 | 0.200 | 0.200 | 0.200 |
|  | Total |  |  | 100.000 |  |  |

Viscosity of the prepared cosmetic compositions was as follows. The viscosity was measured according to the method described in Table 2.

TABLE 2

|  | Example 1 | Example 2 | Example 3 | Example 4 |
|---|---|---|---|---|
| Viscosity (cps) | 60,000 cps (cake type) | 45,000 cps | 23,000 cps | 4,000 cps |
| Measurement method | SUN RHEOMETER CR-500DX Adaptor 25 | BROOKFIELD RVDV-III ULTRA (Serial No. RY6521152) Spindle No. 64, 12 rpm, 30° C., 60 sec | BROOKFIELD RVDV-III ULTRA (Serial No. RY6521152) Spindle No. 64, 12 rpm, 30° C., 60 sec | BROOKFIELD RVDV-III ULTRA (Serial No. RY6521152) Spindle No. 63, 12 rpm, 30° C., 60 sec |

Test Example 1

Measurement of Cosmetic Composition Filling Ability

After impregnating each cosmetic composition in each foam, the ability of filling an adequate amount of the content in given time was evaluated. The filling ability was measured as the time required to fill 15 g of the cosmetic composition.

Test Example 2

Measurement of Cosmetic Composition Impregnating Ability

After filling 15 g of the cosmetic composition in Test Example 1, the amount of the cosmetic composition impregnated in the container was measured.

Test Example 3

Measurement of Cosmetic Composition Discharging Ability

From the foam of Test Example 2, the content was pay-offed with a puff or hand and the ejected amount was measured. The discharging ability was measured as the amount of the cosmetic composition ejected when the cosmetic composition impregnated in the container was applied once using a puff. Compatibility is indicative of the filling ability and means how well the contents having different viscosities are filled in the foam.

The result is as follows.

or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A cosmetic article comprising:
   a puff for discharging a cosmetic composition and applying the cosmetic composition to a skin; and
   a cosmetic composition carrier that comprises a foam having a cell size of 100 to 400 micrometers; where the foam is impregnated with a cosmetic composition according to the following requirements:
   wherein a cosmetic composition having a viscosity of 60000-100000 centipoise (cps) is impregnated in a foam having 10-30 pores per inch (ppi),
   wherein a cosmetic composition having a viscosity of 30000-60000 cps is impregnated in a foam having 30-60 ppi,
   wherein a cosmetic composition having a viscosity of 15000-30000 cps is impregnated in a foam having 60-90 ppi, or
   wherein a cosmetic composition having a viscosity of 1000-5000 cps is impregnated in a foam having 90-130 ppi.

2. The cosmetic composition carrier according to claim 1, wherein the foam comprises one or more selected from a group consisting of butadiene rubber (BR), styrene-butadiene rubber (SBR), natural rubber (NR), wet urethane, dry urethane, polyether, polyester, polyvinyl chloride, polyethylene, ethylene-vinyl acetate (EVA), latex, silicone, styrene-

TABLE 3

|  | Example 1 | Example 2 | Example 3 | Example 4 |
| --- | --- | --- | --- | --- |
| Number of pores per inch (ppi) | 20 ppi | 45 ppi | 75 ppi | 110 ppi |
| Density | 1.8 lb/ft$^3$ | 2.0 lb/ft$^3$ | 2.2 lb/ft$^3$ | 5.3 lb/ft$^3$ |
| Asker F hardness | 10 | 40 | 80 | 100 |
| Cell size (μm) | 350 | 350 | 250 | 150 |
| Image (DSLR camera) |  |  |  |  |
| Description Compatibility | Rough surface High-viscosity (60,000-100,000 cps) content can be impregnated (Pay-off of high-viscosity, high-hardness cake content is controllable) | Rough surface High-viscosity (30,000-60,000 cps) content can be impregnated | Soft Content of viscosity with 15,000-30,000 cps can be impregnated | Dense and soft Low-viscosity (1,000-5,000 cps) content cps can be impregnated |
| Filling ability | Δ | ○ | ○ | Δ |
| Impregnating ability | ○ | ○ | ◉ | ◉ |
| Discharging ability | ○ | ○ | ○ | Δ |

◉: very good, ○: good, Δ: moderate, X: poor

Those skilled in the art will appreciate that the conceptions and specific embodiments disclosed in the foregoing description may be readily utilized as a basis for modifying isoprene-styrene (SIS), styrene-ethylene-butylene-styrene (SEBS), polyvinyl alcohol (PVA), silicone elastomer, nitrile rubber, butyl rubber and neoprene.

3. The cosmetic composition carrier according to claim 1, wherein the foam has a thickness of 5-30 mm.

4. The cosmetic composition carrier according to claim 1, wherein the foam has a hardness of 10-120 being measured with a durometer before the cosmetic composition is impregnated.

5. The cosmetic composition carrier according to claim 1, wherein the foam is flocked with cotton, cotton/acryl, cotton/acryl/polyester, cotton/rayon, acryl, polyamide, nylon, polyester, nylon/polyester or silk.

6. The cosmetic composition carrier according to claim 5, wherein the foam is flocked with a fiber of 0.6-1.5 Denier and 0.6-1.0 mm.

7. The cosmetic composition carrier according to claim 1, wherein the cosmetic composition is in liquid or solid state.

8. The cosmetic composition carrier according to claim 1, wherein the cosmetic composition is solution, emulsion, gel, cream or suspension.

* * * * *